United States Patent [19]

Sherman et al.

[11] Patent Number: 5,057,112
[45] Date of Patent: Oct. 15, 1991

[54] PNEUMATICALLY POWERED ORTHOPEDIC BROACH

[75] Inventors: Randy G. Sherman; Marc Vreede; Fred D. Tripp, all of Austin, Tex.

[73] Assignee: Intermedics Orthopedics, Inc., Austin, Tex.

[21] Appl. No.: 460,828

[22] Filed: Jan. 4, 1990

[51] Int. Cl.⁵ .............................................. A61B 17/16
[52] U.S. Cl. ......................................... 606/79; 606/86; 606/100
[58] Field of Search ........................ 606/79, 80, 86, 96, 606/100, 104

[56] References Cited

U.S. PATENT DOCUMENTS

| | | | |
|---|---|---|---|
| 2,740,406 | 4/1956 | Tofflemire | 606/79 |
| 3,752,161 | 8/1973 | Bent | 606/79 |
| 4,273,117 | 6/1981 | Neuhäuser | 606/80 |
| 4,298,074 | 11/1981 | Mattchen | 606/104 |
| 4,696,292 | 9/1987 | Heiple | 606/79 |
| 4,736,742 | 4/1988 | Alexson et al. | 606/80 |
| 4,782,833 | 11/1988 | Einhorn et al. | 606/80 |
| 4,895,146 | 1/1990 | Draenert | 606/79 |
| 4,919,679 | 4/1990 | Averill | 623/23 |

FOREIGN PATENT DOCUMENTS 8900059 7/1989 European Pat. Off. .
0144005 6/1985 Switzerland .

OTHER PUBLICATIONS

Allo Pro Brochure.

*Primary Examiner*—Stephen C. Pellegrino
*Assistant Examiner*—Michael Rafa
*Attorney, Agent, or Firm*—John R. Merkling

[57] ABSTRACT

A pneumatically driven orthopedic broach inserter comprising a continuously reciprocating piston which strikes a proximal anvil during each cycle. The impact of the piston with the proximal anvil drives the broach out of a bone. To drive the broach into the bone, a surgeon pushes on the power broach inserter, bringing a distal anvil into the path of the piston, and creating a forward action which dominates over the on-going reverse action produced by the piston striking the proximal anvil. The piston is provided with a low-friction sleeve so that completely oilless operation is possible. A fast-acting chuck having a key and a wedge is provided whereby broaches of different size can be quickly attached to the power broach inserter. In addition, means whereby the relative angular orientation between the broach and the power broach inserter may be changed continuously as the surgeon presents the broach toward the bone, but whereby the angular orientation is fixed as the surgeon pushes the broach into the bone is provided.

33 Claims, 6 Drawing Sheets

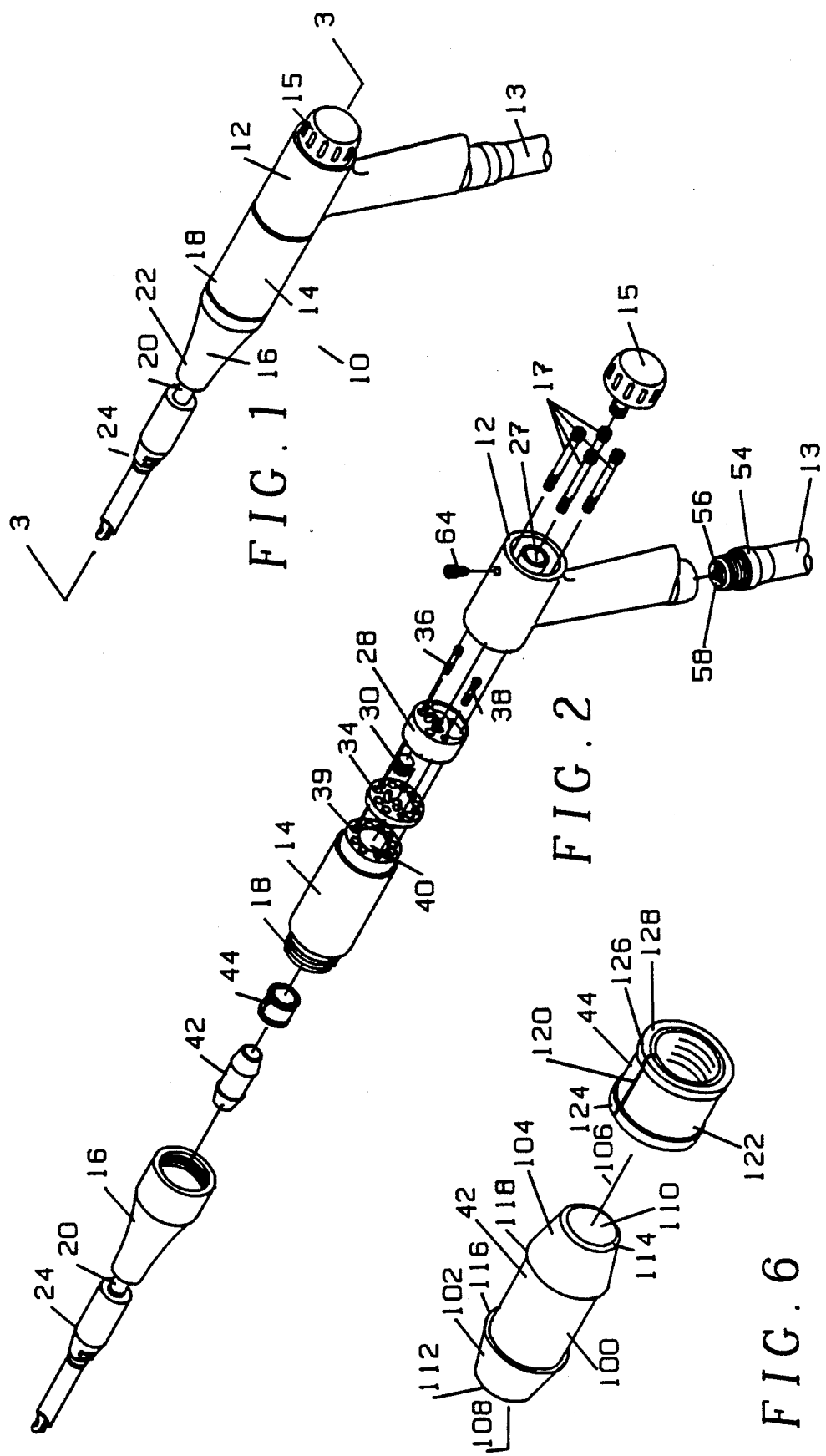

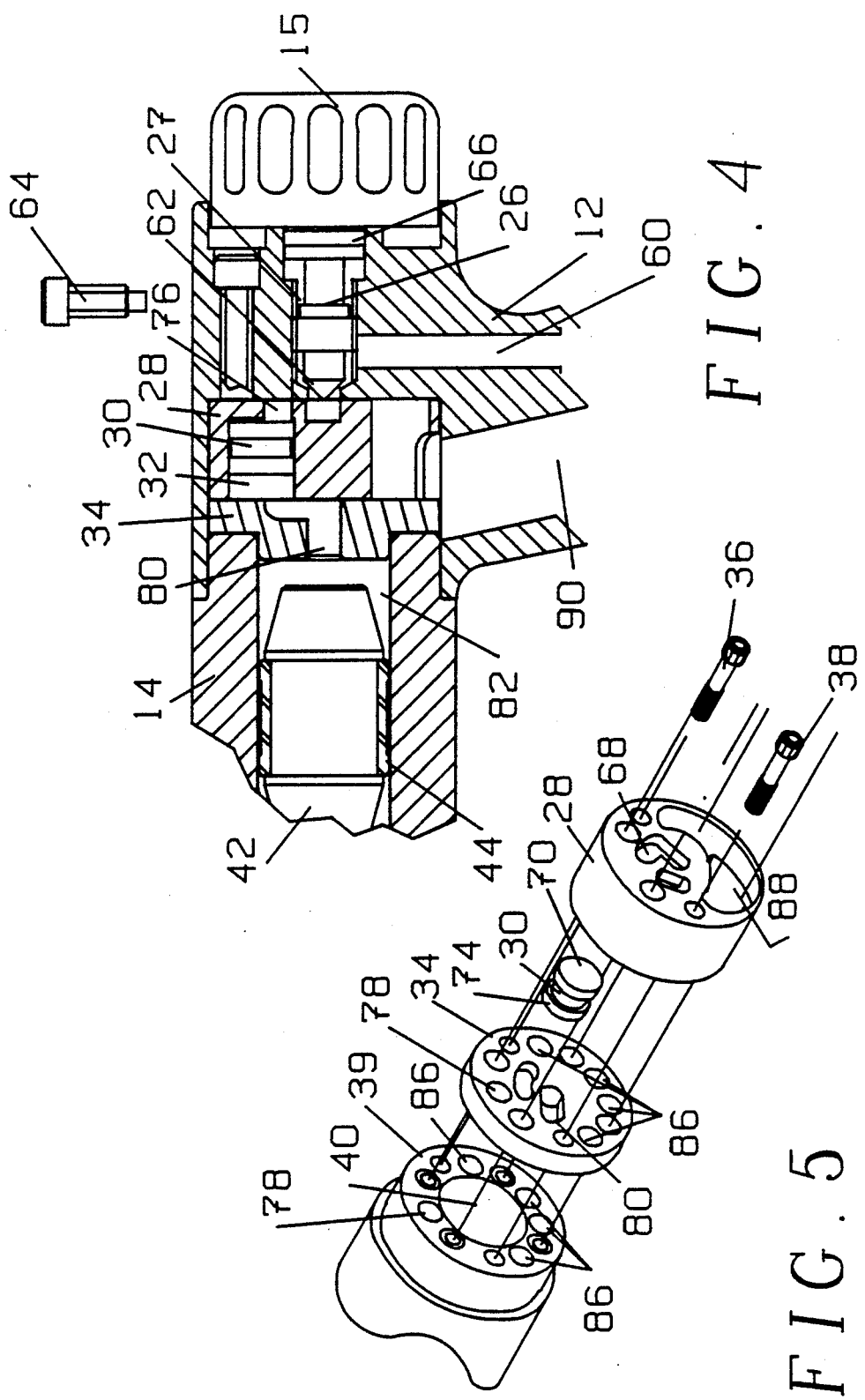

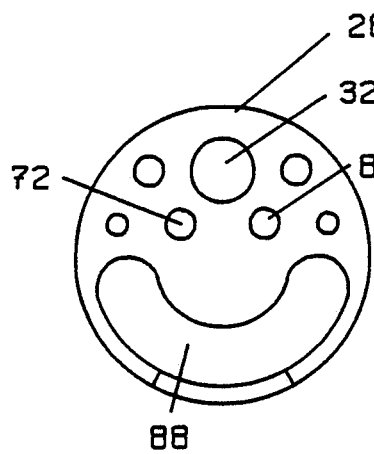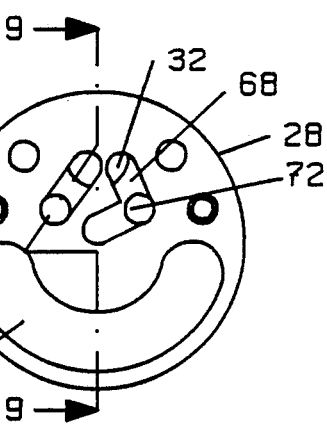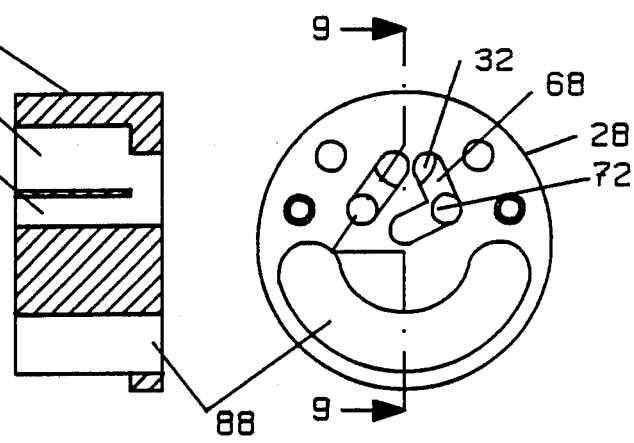
FIG.10   FIG.9   FIG.8
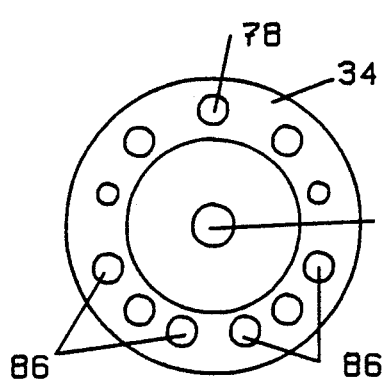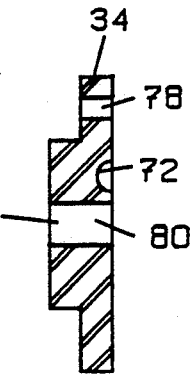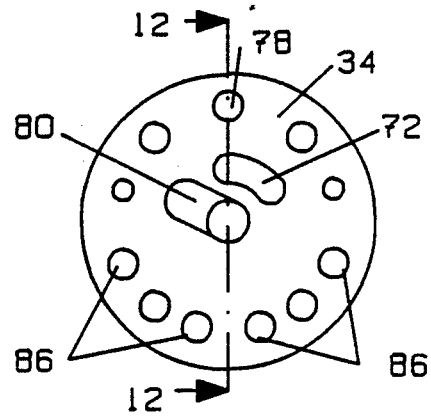
FIG.13   FIG.12   FIG.11

PNEUMATICALLY POWERED ORTHOPEDIC BROACH

TECHNICAL FIELD

Our invention relates to devices for orthopedics surgery, and in particular to broaches for creating cavities in bone for receiving orthopedic implants, such as artificial hips.

BACKGROUND OF THE INVENTION

Artificial joints, such as an artificial hip, are often attached to a structurally sound bone by a stem lodged in a cavity formed in the bone. To create the cavity, a surgeon may remove worn or diseased bone structure and then drill and hollow out a cavity along the medullary canal of the bone. The cavity is ultimately shaped to accommodate the stem of the prosthesis. The prosthesis is secured in place by a combination of cement, pressure between the bone and the prosthesis, or mechanical structure such as screws or pins. If the cavity conforms to the shape of the stem, a better implant can be expected.

To create the cavity, a surgeon may use a shaped broach which conforms to the shape of the prosthesis stem. In the past, the broach has been mounted on a handle and hammered into the bone. This is an arduous procedure, which relies greatly on the skill and strength of the surgeon. Some variation in the strength and direction of the applied blows is inevitable, and this results in variation in size and placement of the cavity. Moreover, the force required for the operation, coupled with a wedge-shaped broach, will sometimes split the bone.

To overcome some of these disadvantages, power rasps have been proposed, such as one produced by Allo Pro. The Allo Pro power rasp is pneumatically driven with a trigger-operated hand control and a switched valve for forward and reverse operation. We believe, however, that there is still a need for a pneumatically powered orthopedic broach with ergonometric control.

SUMMARY OF THE INVENTION

We have invented a pneumatically driven orthopedic power broach inserter which does not require a switch to operate in forward or reverse action. Moreover, no trigger is required to regulate the force delivered. The power broach inserter comprises a continuously reciprocating piston which strikes a proximal anvil during each cycle. The impact of the piston with the proximal anvil tends to drive the power broach inserter towards the surgeon operating the inserter and to withdraw the broach out of the bone. To drive the broach into the bone, the surgeon merely pushes on the power broach inserter. This action brings a distal anvil into the path of the piston, creating a forward action which dominates over the on-going reverse action produced by the piston striking the proximal anvil. Moreover, we have found that the residual withdrawing action retracts the broach briefly during each cycle, permitting bone chips to be flushed out of the cavity without removing the broach from the cavity.

The piston is provided with a low-friction sleeve so that completely oilless operation is possible. Oil is a potential contaminant in an operating room environment and presents problems for sterilization. We have discovered, however, that some frictional losses are needed to produce the desired piston action without instability in the action of the piston.

We have also invented a fast-acting chuck whereby broaches of different size can be quickly attached to the power broach inserter. We have found that a key and wedge can create a sufficiently stabile attachment between the power broach inserter and a broach.

In addition, we have provided means whereby the relative angular orientation between the broach and the power broach inserter may be changed continuously as the surgeon presents the broach toward the bone, but whereby the angular orientation is fixed as the surgeon pushes the broach into the bone. This feature is achieved without external controls which would need to be manipulated by the surgeon.

With the foregoing in mind, it is an object of the present invention to provide a pneumatically powered broach inserter, having improved ergonometric control.

Another important object of the invention is to provide a power broach inserter having a normal mode of operation which tends to extract a broach out of bone. A further object of the present invention is to provide a power broach inserter which can be shifted from reverse to forward action and back to reverse action without manipulation of controls.

Another important principal of our invention is to provide a power broach inserter with a fast-action chuck which can rapidly accommodate a exchange of broaches mounted on the power broach inserter.

Another object is to provide a fast-acting chuck which can rigidly mount a broach on the power broach inserter.

It is another object of our invention to provide a means whereby the angular orientation of the broach with respect to the power broach inserter can be changed as the broach is presented to bone, but whereby the orientation becomes fixed as the broach is driven into the bone. It is also an object of our invention to provide the aforesaid means without the requirement of external controls.

These and other objects and advantages of our invention will be apparent from the accompanying drawings and detailed description of our preferred embodiment.

BRIEF DESCRIPTION OF THE DRAWINGS

FIG. 1 is a perspective view of a power broach inserter according to our invention;

FIG. 2 is an exploded view of the power broach inserter of FIG. 1;

FIG. 4 is an enlarged portion of the view of FIG. 3;

FIG. 5 is an enlarged exploded view of a shuttle valve assembly;

FIG. 6 is an enlarged exploded view of a piston and sleeve;

FIG. 8 is a plan view of a proximal side of a manifold of the power broach inserter;

FIG. 9 is a through section of the manifold of FIG. 3 taken along broken line 9—9;

FIG. 10 is a plan view of a distal side of the manifold of FIG. 8;

FIG. 11 is a plan view of a proximal side of a proximal anvil;

FIG. 12 is a through section of the anvil taken along line 12—12 of FIG. 11;

FIG. 13 is a plan view of a distal side of the anvil of FIG. 11;

DETAILED DESCRIPTION OF A PREFERRED EMBODIMENT

Figure 3:
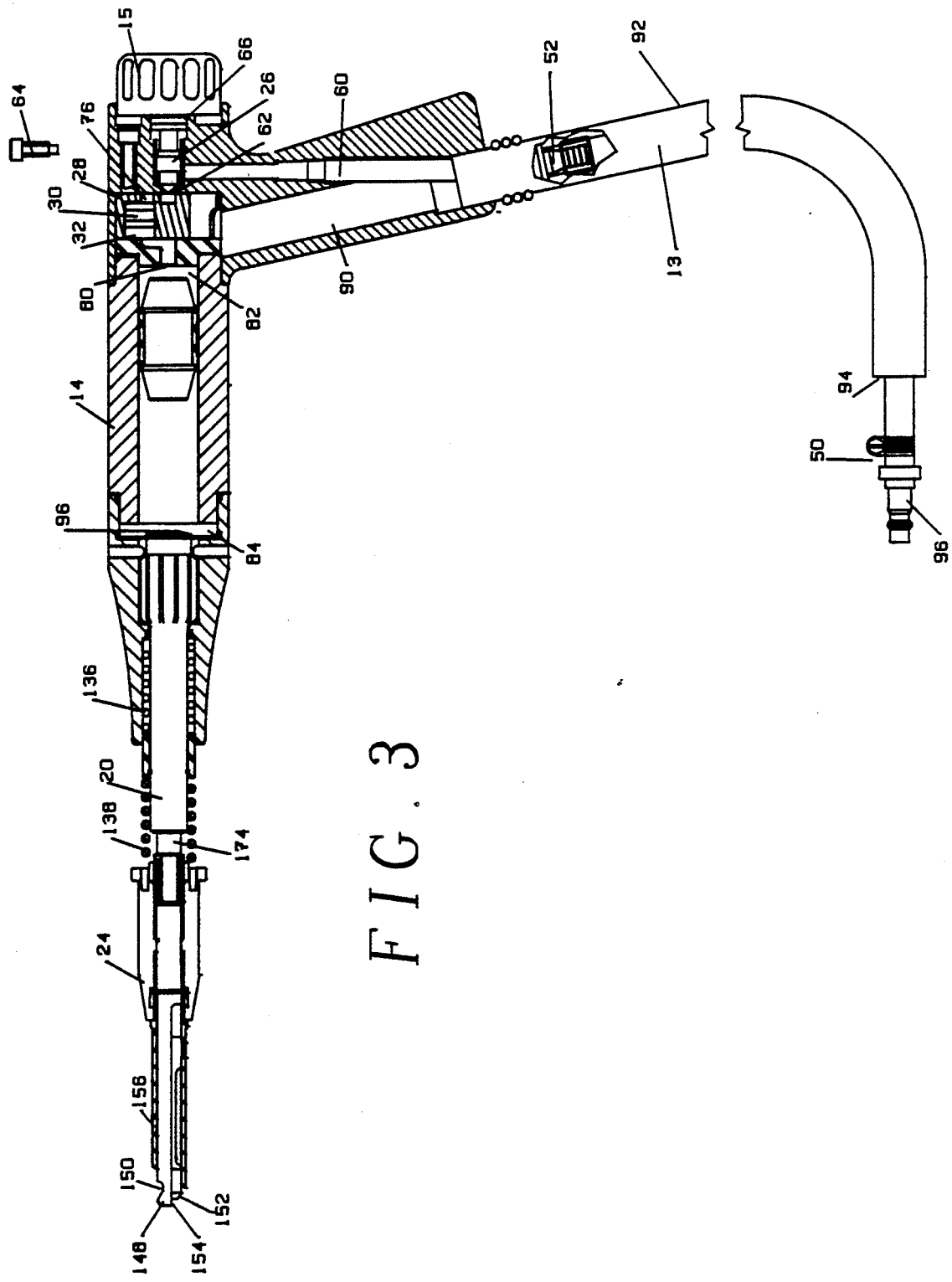
FIG. 3 is a sectional view of the power broacher inserter taken along line 3—3 of FIG. 1.

Reference is now made to the figures wherein like numerals designate like parts throughout. In FIG. 1, a perspective view of a power broach inserter, generally designated 10, is shown. The power broach inserter 10 comprises a handle 12 to which an air hose 13 is attached. The handle 12 also supports a cylinder assembly 14, which is attached to the handle 12 by four screws 17. A flow control knob 15 is mounted on the handle 12 to adjust the air flow. A nose assembly 16 is attached to a distal end 18 of the cylinder assembly 14. A shaft 20, protruding from a distal end 22 of the nose assembly 16, carries a broach connector 24, the function of which will be more fully explained below in connection with FIG. 7.

The power broach inserter 10 is shown in an exploded view in FIG. 2. In FIG. 2 it can be seen that the control knob 15 manipulates a threaded needle valve 26 which engages a threaded bore 27 in the handle 12. As will be more fully explained below, low pressure gases, preferably either nitrogen or air, pass through the air hose 13, into the handle 12, past the needle valve 26 and into a manifold 28. A shuttle valve 30 oscillates in a chamber 32 in the manifold 28. The manifold 28 abuts a proximal anvil or an anvil plate 34. Both the anvil plate 34 and the manifold 28 have air passages for controlling the flow of air in the power broach inserter 10.

Figure 14:
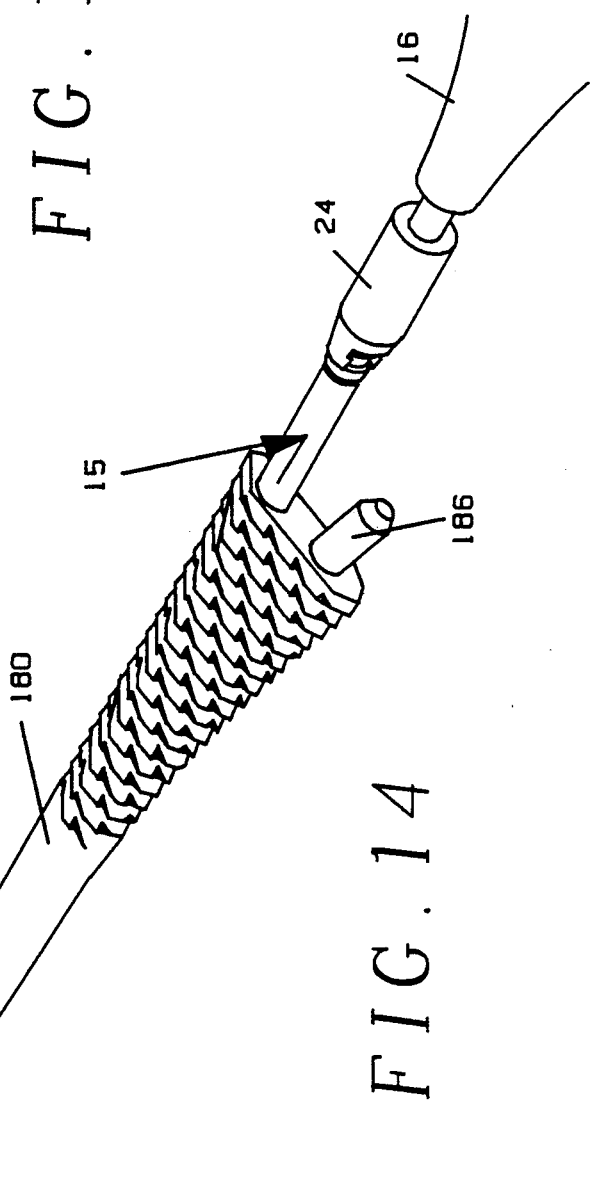
FIG. 14 is a perspective view of the chuck assembly showing a broach mounted thereon.

Two screws 36, 38 secure the manifold 28 and the anvil plate 34 to a proximal face 39 of the cylinder assembly 14. There is a main cylinder 40 in the cylinder assembly 14. A piston 42 reciprocates in the main cylinder 40 and provides impacts by which a broach, such as broach 180 in FIG. 14, can be driven into bone by the power broach inserter 10. A piston sleeve 44 fits over the piston 42 to provide a low friction sliding contact with the main cylinder 40.

For a detailed explanation of the action of the power broach inserter 10, reference is now made to FIGS. 3, 4 and 5. For operation, the power broach inserter 10 requires a low pressure, high volume gas supply, for example, nitrogen which is commonly available in operating rooms. A male quick-connect 46 is provided to connect the power broach inserter 10 to the air supply or to a foot valve (not shown) for regulating the air flow. An inlet hose 48, attached to the quick-connect 46 with a hose clamp 50, carries low pressure gas to a male fitment 52. The fitment 52 is part of a threaded connector 54 which has an inner inlet passage 56 and an outer exhaust passage 58, as seen in FIG. 2. The inner inlet passage 56 communicates with an inlet flow line 60, which carries the gas to the needle valve 26. The needle valve 26 controls the volume of air available to the power broach inserter 10. Rotating the control knob 16 moves the needle valve 26 along the threaded bore 27 and opens or closes the valve through proximity to a valve seat 62. A dog point screw 64 is used to prevent the needle valve 26 from being completely removed from the power broach inserter 10. An O-ring 66 prevents gases from escaping from the valve 26 around the control knob 16. Gases which pass through the valve 26 are conducted through the manifold 28 and the anvil plate 34 to both ends of the shuttle valve 30. As will be described hereafter, the reciprocating action of the shuttle valve 30 cooperates with a related reciprocating action of the piston 42 to provide a stable oscillation which can be used to drive a broach into a bone.

Gases entering the manifold 28 are conducted through a V-shaped passage 68 to a proximal side 70 of the shuttle valve 30 and simultaneously through a distal inlet 72 to a distal side 74 of the shuttle valve 30. The cyclic action of the shuttle valve 30 and the piston 32 will now be explained beginning with an arbitrarily chosen starting condition shown in FIG. 4. As seen in FIG. 4, the shuttle 30 is displaced proximally in the manifold 28. In this position, the shuttle valve 30 seals a shuttle valve proximal inlet 76 from the V-shaped passage 68 and prevents gases from flowing into a proximal piston inlet 80. At the same time gases flow into the shuttle valve distal inlet 72 and through a distal piston inlet 78. Pressures on the proximal and distal sides of the shuttle valve 30 are substantially the same, so the shuttle valve will not move until there is a change of pressure. To the extent that the pressure on the proximal side of the shuttle valve 30 is greater than the pressure on the distal side of the shuttle valve, the forces are nevertheless balanced because a greater area of the distal side of the valve 30 is exposed to the gas pressure when compared to the area of the proximal side of the shuttle valve.

With the shuttle valve 30 in the position shown, pressurized gas flows through the proximal piston inlet 80 and begins to drive the piston 42 forward along the main cylinder 40 and away from a proximal end 82 of the main cylinder 40. There is little or no back pressure in a distal end 84 of the main cylinder 40 because that portion of the cylinder 40 is vented to ambient through four exhaust ports 86. The exhaust ports 86 open into the main cylinder 40 substantially midway along the cylinder. The exhaust ports 86 carry gases along the cylinder assembly 14, through the anvil plate 34 and into an exhaust chamber 88 in the manifold 28. From the exhaust chamber 88, gases are conducted through a passage 90 in the handle 12 and into an exhaust hose 92 which is part of the air hose 13. The exhaust hose 92 surrounds the inlet hose 48 so that exhaust gases pass along the outside of the inlet hose to a point near the quick-connect 46. At an open end 94 of the exhaust hose 92, the gases are vented to ambient. In an operating room environment, exhausted gases must be carried away from the field of operation. Coaxial inlet and outlet hoses accomplish this requirement without multiple lines entering or leaving the operating field.

Returning now to the description of the action of the shuttle valve 30 and the piston 42, the pressurized gases passing through the piston proximal inlet 80 drive the piston forward along the main cylinder 40. As the piston moves down the cylinder, it passes over the openings of the exhaust ports 86. The proximal end of the cylinder 40 is then vented to ambient and a loss of pressure occurs both in the proximal end of the main cylinder and on the distal side of the shuttle valve 30. Because the shuttle valve 30 is of low mass and has a short distance to travel, it is rapidly driven away from the proximal side of the manifold 28 and against the anvil plate 34. Pressurized gases are then conducted through the V-shaped passage 68 and the shuttle valve distal inlet 72, then along the piston distal end inlet 78 to the distal end of the main cylinder 40. Pressurization of the distal end of the main cylinder slows the forward motion of the piston 42 and reverses it. As will be more fully explained below, if the components of the power broach inserter 10 are in the position shown in FIG. 4, the piston 42 does not strike a distal or movable anvil 96 on the shaft 20. The motion of the piston 42 is reversed and the piston moves along the cylinder 40 toward the proximal end of the cylinder. As the piston 42 passes over the exhaust ports 86, there is a pressure loss in the distal end of the main cylinder 40. This pressure loss unbalances the pressures on the shuttle valve 30 and drives it back against the proximal side of the manifold 28, into the position shown in FIG. 3. On the return stroke of the piston 42, however, the piston 42 strikes the face of the anvil plate 34. In the preferred embodiment of our invention, therefore, the normal condition of the power broach inserter 10 tends to extract the a broach out of a bone. To drive the broach into bone, a physician must push on the power broach inserter 10 as will be explained below. The anvil Plate 34 is made of a resilient, preferably non-metallic substance, such as polyetheretherketone, commonly called "PEEK". The resiliency of the anvil plate 34 permits a plastic impact between the piston 42 and the plate 34.

The piston 42 and sleeve 44 are illustrated particularly in FIG. 6. The piston comprises a central barrel 100 with a distal end 102 and a proximal end 104. The piston 42 is symmetrical around an axis 106 and the two ends 102, 104 are mirror images of each other. Both the distal end 102 and the proximal end 104 form frustroconical shapes and define striking faces 108 and 110 respectively. The striking faces 108, 110 are chamfered at edges 112, 114. Adjacent the central barrel 100, each end 102, 104 forms a lip 116, 118, which holds the sleeve 44 on the piston 42.

In a medical device for use in a operating room environment such as the power broach inserter 10, it is important to provide for sterilization of the device. Oil, sometimes used as a lubricant, can impede sterilization and can itself be a contaminant in the operating room. An important part of our invention, therefore, is the low friction sleeve 44 which permits oilless operation of the power broach inserter 10. The sleeve 44 is made of poly(amide-imide). This composite comprises a graphite or carbon powder imbedded in a matrix, which produces a low co-efficient friction. A suitable substance is Torlon, manufactured by AMOCO. However, we have also found that extremely low friction is also to be avoided. A certain amount of friction is needed to limit the acceleration and maximum velocity of the piston. This permits the motion of the piston 42 to be reversed, provides a greater dwell of the piston on the anvils 34, 96 so that more energy is transferred to do work, and diminishes lateral vibration, or "canting", of the piston. AMOCO reports a 0.2 co-efficient of dynamic friction for its Torlon 4301 against steel. The main cylinder 40 in our power broach inserter is comprised of anodized aluminum. We provide a semipolished surface on the interior of the cylinder. The surface is lightly abraded to remove prominences, but a highly polished finish is not desireable. The interaction of the sleeve and cylindrical surface damps the motion of the piston to produce the benefits described above.

The sleeve 44 fits over the piston 42. A slot 120 makes it possible to force the sleeve on to the piston 42 where it will fit securely between the lips 116, 118. A central portion 122 of the sleeve is recessed so that a ring 124, 126 can be formed at each end of the sleeve 44. The outer corners of the rings 124, 126 are chamfered 128. The rings 124, 126 present relatively small surface areas for contact with the main cylinder 40. At the same time, the rings are spaced apart so that the piston 42 does not rock in the cylinder 40. Using this configuration, the power broach inserter 10 can be operated without a lubricant such as oil. Some blow by of gases past the sleeve 44 is to be expected, but since the driving gases are supplied at relatively low pressure but high volume, the losses are not significant.

As mentioned above, the piston 42 normally strikes the anvil 34 in each cycle, but does not ordinarily strike the moveable anvil 96. This action tends to extract the broach out of bone, rather than driving the broach into the bone. This feature tends to ensure that the broach will be driven into bone only in response to a purposeful action by a surgeon. Impact forces from the piston 42 are transmitted to the broach through the shaft 20 as will be explained now with reference to FIG. 7. The shaft 20 protrudes from the nose assembly 16. The moveable anvil 96 is located at a proximal end of the shaft 20. In order to drive the broach into the bone, the surgeon would push the power broach inserter 10 forward, as if pushing the broach into the bone. This action would compress a spring 136 mounted along the shaft 20, forcing the moveable anvil 96 into the path of the reciprocating piston 42. Because the interaction between the moveable anvil 96 and piston 42 affects the motion of the piston, there is a certain condition where maximum force is transmitted from the piston to the shaft 20. Should a surgeon push harder on the power broach inserter 10, the effective transmitted power would be reduced. The power broach inserter 10, therefore, tends to regulate the speed at which the broach can be advanced into bone, to minimizing the possibility that the bone might split during the broaching procedure.

When the broach is driven into the bone by an impact of the piston 42 against the moveable anvil 96, the broach breaks off small chips of bone and pulverizes them. The piston 42 then strikes the anvil plate 34 which extracts the broach out of the bone a small distance. In the space thus formed between the bone and the broach, the pulverized bone mixes with blood and body fluids to form a slurry. As the broach is forced forward by the surgeon's pushing action and by the next impact of the piston 42 against the moveable anvil 96, the slurry is forced out of the cavity being created by the broach. The power broach inserter 10, therefore, continuously removes debris from the bone cavity, eliminating the need to withdraw the broach and clean the cavity.

Figure 7:
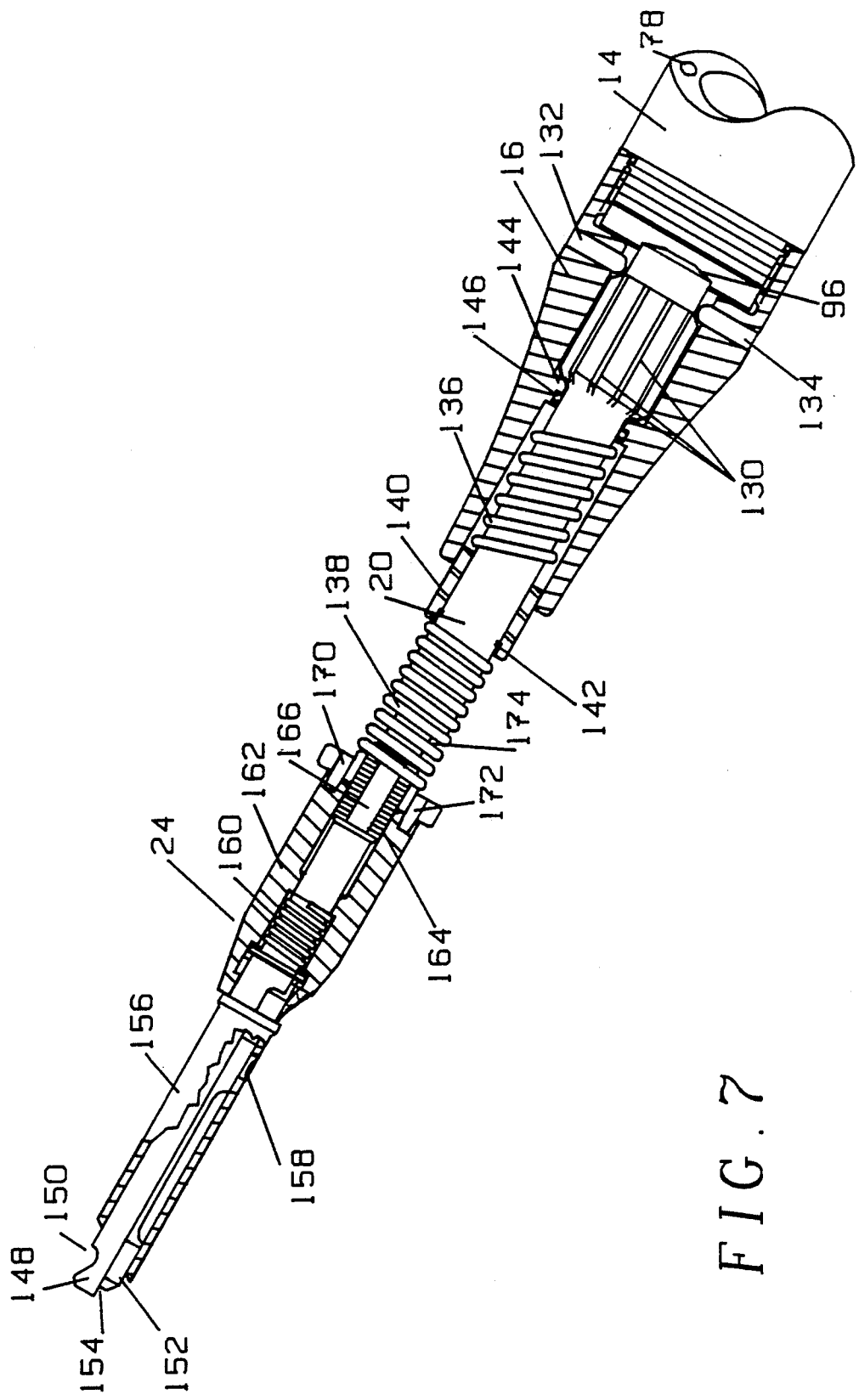
FIG. 7 is an enlarged portion of the through sectional view of FIG. 3, showing a chuck assembly.
Figure 15:
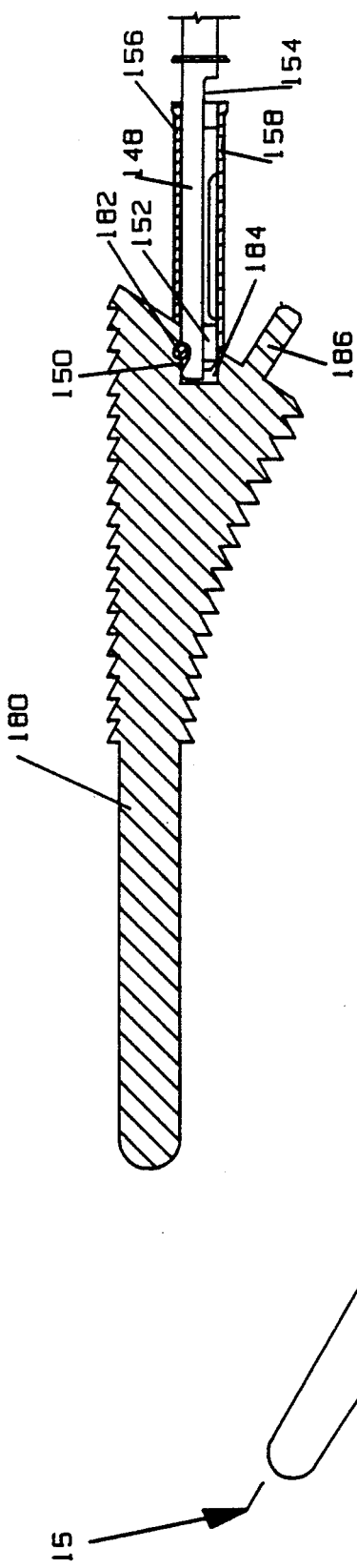
FIG. 15 is a through section view of a portion of the chuck assembly and broach of FIG. 14, taken along line 15—15.

As seen in FIG. 7, immediately adjacent to the moveable anvil 96, there are a plurality of splines 130 on the shaft 20. The splines 130 are configured to engage pins 132, 134 which are mounted in the nose assembly 16. When the shaft is extended, as shown in FIG. 7, the shaft 20 can be freely rotated. This permits the surgeon to adjust the configuration of the power broach inserter 10 so that the broach can be driven into the bone easily. As the surgeon presses on the power broach inserter 10, the shaft 20 is forced further into the nose assembly 16 and the splines 130 engage the pins 132, 134 so that the relative positions of the broach and the inserter 10 are fixed rotationally before the piston 42 begins striking the moveable anvil 96.

A spring 136 holds the shaft 20 in a normally extended position. The spring 136 presses against a plastic sleeve 140 which is held in position on the shaft 120 by a split ring clip 142. The plastic sleeve 140 can slide in the nose assembly 16 and provides lateral support for the shaft 20. A ridge 144 on the interior of the nose assembly 16 also supports the shaft 20 laterally. An O-ring 146 in the ridge 144 seals the shaft 20 to prevent excessive escape of the gases used to power the inserter 10.

The connector assembly 24 at the end of the shaft 20 grips the broach during the insertion process. The connector assembly 24 comprises a key 148 at the end of the shaft 20. The key 148 has an indentation 150 which is adapted to engage a pin 182 in a specially provided cavity 184 in the broach 180. A pin 152 slides along a flattened undersurface 154 of the key 148. A sleeve 156 surrounds both the key 148 and the pin 152 and the pin 152 is attached to the sleeve 156 by a spot weld 158. When the key 148 is inserted into the broach, the sleeve 156 and pin 152 can be forced against the broach, wedging the key 148 and broach together. A second spring 160 pushes the sleeve 156 and the pin 152 forward so that the connector 24 ordinarily grips the broach.

After the broach 180 has been placed on the key 148 and pin 152, the inserter 10 and the broach can be locked together by the action of a chuck 162 which tightens on a threaded portion 164 of the shaft 20. The threaded portion 164 has two opposing flats, one flat 166 being shown in FIG. 7, for engaging a lock ring 168. Because the vibrating action of the inserter 10 tends to loosen the chuck 162, a positive locking mechanism is provided in the preferred embodiment. The locking mechanism comprises the lock ring 168 which has a rectangular central bore (not shown). Opposing sides of the central bore are adapted to engage the flats 166 on the threaded portion 164 of the shaft 20. Pins, such as pins 170 and 172 are mounted in the lock ring 168 and engage holes in a proximal side of the chuck 162. In the preferred embodiment three pins, such as pins 170, 172, are provided, while twenty-one holes may be provided. This permits the chuck 162 to be locked with very little play. To adjust the chuck 162, the lock-ring 168 is pulled back against a spring 138 to a relieved portion 174 on the shaft 20. The relieved portion 174 is best seen in FIG. 3. The lock-ring 168 can then be turned 90 degrees so that it is caught temporarily in the relieved portion 174. Once the chuck 162 has been tightened, the lock-ring 168 can be turned and slid into position against the proximal end of the chuck 162.

The connector assembly 24 can also be used with conventional hammer-driven broach inserters or with other powered devices.

With the broach secured to the connector 24 and the air supply regulated through the needle valve 26, the surgeon would place the broach against the end of a bone and press on the inserter 10 as if pushing the broach into the bone. This action would compress the spring 136 and bring the moveable anvil 96 within the range of motion of the piston 42. The inserter 10 would then begin to drive the broach into the bone at a speed proportional to the pressure applied by the physician. If, however, excess pressure were applied, the moveable anvil 96 would begin to interfere with the motion of the piston 42 and the cutting action of the broach would be slowed. When the physician stops pushing on the inserter 10, the piston 42 continues to strike the anvil plate 34, thus tending to extract the broach out of the bone. The broach, therefore, can be easily removed from the bone after the desired depth of cut has been obtained.

In our preferred embodiment, after the broach 180 has been driven into the bone, the power broach inserter 10 can be temporarily removed from the broach and a circular planer (not shown) can be slid onto a support pin 186. The planer will create a flat surface on the bone for engaging a shoulder on a prosthesis, as shown, for example, in U.S. Pat. No. 3,813,699 to Gilberty.

Our invention may be embodied in other specific forms without departing from the spirit or teachings of the present invention. All embodiments, therefore, which come within the meaning and range of the doctrine of equivalence are intended to be included herein and the scope of the invention should be determined by the appended claims, and not by the forgoing description.

We claim as our invention:

1. An apparatus for driving an orthopedic broach into a bone of a patient, comprising:
   means for mounting a broach on the apparatus,
   means continually operative to apply a periodic percussive force to the broach in a first direction,
   means selectively operative to apply a second periodic percussive force to the broach in a second direction, said second direction being substantially opposite to said first direction, and
   means for controlling the magnitude of the second percussive force applied by selectively operative means.

2. The apparatus according to claim 1 wherein the continually operative force-applying means further comprises:
   retracting means and
   proximal anvil means, said retracting means striking said anvil means during substantially each cycle of operation of the apparatus.

3. The apparatus according to claim 2 wherein the selectively operative force-applying means further comprises:
   inserting means and
   a distal, moveable anvil means, said distal anvil means being connected to the broach mounting means, and
   means for displacing the moveable anvil means into the path of the inserting means.

4. The apparatus according to claim 3, wherein the anvil displacing means comprise:
   a shaft connected at one end thereof to the broach mounting means and at an other end thereof to the moveable anvil means, and
   spring means tending to hold the shaft away from the inserting means.

5. The apparatus according to claim 4 wherein the retracting means comprise a proximal face of a piston and wherein the inserting means comprise a distal face of a piston.

6. The apparatus according to claim 5 wherein the piston comprises means for providing a low-friction sliding surface without a lubricant.

7. The apparatus according to claim 6 wherein the surface providing means comprise a polyamide-imide sleeve.

8. The apparatus according to claim 7 wherein the polyamideimide sleeve further comprises a first ridge at a proximal end of the sleeve, and a second ridge at a distal end of the sleeve.

9. The apparatus according to claim 8 further comprising a semi-gloss surface engaging the sliding surface of the piston.

10. The apparatus according to claim 9 further comprising means for selectively rotating the broach mounting means.

11. The apparatus according to claim 10 wherein the rotating means comprise means for permitting rotation of the broach mounting means during operation of the continually operative force applying means as long as the inserting force applying means is not selected and means for prohibiting rotation of the broach mounting means when the inserting force applying means is selected.

12. The apparatus according to claim 11 wherein the rotation prohibiting means comprise a plurality of splines on the shaft and at least one pin for selectively engaging at least one of the splines, whereby rotation of the shaft is prevented.

13. The apparatus according to claim 12 wherein the splines are parallel to an axis of the shaft.

14. The apparatus according to claim 13 wherein the splines extend radially from the shaft.

15. The apparatus according to claim 14 wherein the rotation permitting means comprise a sleeve mounted on the shaft.

16. The apparatus according to claim 15 wherein the broach mounting means comprise
means for gripping a pin in a bore in a broach, and
means for wedging the gripping means against the ridge.

17. The apparatus according to claim 16 wherein the wedging means further comprise means for insertion into the bore in the broach and a sleeve surrounding the gripping means and the insertion means.

18. The apparatus according to claim 17 wherein the sleeve comprises an inclined end for pushing against the broach.

19. The apparatus according to claim 18 wherein the broach mounting means further comprise chuck means for tightening the insertion means into the broach and for tightening the inclined end of the sleeve against the broach.

20. The apparatus according to claim 19 wherein the chuck means further comprise means for locking the chuck means in a tightened position.

21. The apparatus according to claim 20 wherein the locking means comprise a pair of opposed flats on the shaft and a lock ring having a central opening with at least two surfaces for engaging the opposed flats and means for connecting the lock ring and the chuck means.

22. The apparatus according to claim 21 wherein the connecting means comprise at least one pin on the lock ring and a plurality of opposed bores in the chuck means.

23. The apparatus according to claim 4 further comprising means for selectively rotating the broach mounting means.

24. The apparatus according to claim 23 wherein the rotating means comprise means for permitting rotation of the broach mounting means during operation of the continually operative force applying means as long as the inserting force applying means is not selected and means for prohibiting rotation of the broach mounting means when the inserting force applying means is selected.

25. The apparatus according to claim 24 wherein the rotation prohibiting means comprise a plurality of splines on the shaft and at least one pin for engaging at least one of the splines, whereby rotation of the shaft is prevented.

26. The apparatus according to claim 25 wherein the splines are parallel to an axis of the shaft.

27. The apparatus according to claim 26 wherein the splines extend radially from the shaft.

28. The apparatus according to claim 27 wherein the rotation permitting means comprise a sleeve mounted on the shaft.

29. An apparatus for driving an orthopedic broach into a patient's bone, comprising:
means for mounting a broach on the apparatus,
means for producing a periodic percussive force,
means for selectively applying said force to the broach,
means for permitting rotation of the broach mounting means, whenever said periodic percussive force is being produced but is not applied to the broach and
means for prohibiting rotation of the broach mounting means whenever said force is applied to the broach.

30. The apparatus according to claim 29 further comprising a shaft connected to said mounting means and slidable axially with respect to the force producing means and wherein the rotation prohibiting means comprise a plurality of splines on the shaft and at least one pin for selectively engaging at least one of the splines, whereby rotation of the shaft is prevented.

31. The apparatus according to claim 30 wherein the splines are parallel to an axis of the shaft.

32. The apparatus according to claim 31 wherein the splines extend radially from the shaft.

33. The apparatus according to claim 32 wherein the rotation permitting means comprise a sleeve mounted on the shaft.

* * * * *